(12) United States Patent
Lee

(10) Patent No.: US 8,005,186 B2
(45) Date of Patent: Aug. 23, 2011

(54) COMPLEX IMAGING SYSTEM FOR DENTAL

(75) Inventor: Sang Chul Lee, Gyeonggi-do (KR)

(73) Assignee: Ray Co., Ltd., Gyeonggi-Do (KR)

( * ) Notice: Subject to any disclaimer, the term of this patent is extended or adjusted under 35 U.S.C. 154(b) by 95 days.

(21) Appl. No.: 12/442,136

(22) PCT Filed: Sep. 21, 2007

(86) PCT No.: PCT/KR2007/004667
§ 371 (c)(1),
(2), (4) Date: Mar. 20, 2009

(87) PCT Pub. No.: WO2008/035953
PCT Pub. Date: Mar. 27, 2008

(65) Prior Publication Data
US 2009/0245461 A1    Oct. 1, 2009

(30) Foreign Application Priority Data
Sep. 22, 2006  (WO) ................ PCT/KR2006/003763

(51) Int. Cl.
A61B 6/14    (2006.01)
G01N 23/083  (2006.01)

(52) U.S. Cl. ................ 378/38; 378/13; 378/20; 378/39

(58) Field of Classification Search ................ 378/4–20, 378/38–40; 433/215, 229, 68, 29; D24/107, D24/158–161
See application file for complete search history.

(56) References Cited

U.S. PATENT DOCUMENTS

| | | | | |
|---|---|---|---|---|
| 4,365,340 A | * | 12/1982 | Nishikawa et al. | 378/39 |
| 4,788,699 A | * | 11/1988 | Dobert et al. | 378/38 |
| 5,058,147 A | * | 10/1991 | Nishikawa et al. | 378/38 |
| 5,511,106 A | * | 4/1996 | Doebert et al. | 378/146 |
| 6,118,842 A | * | 9/2000 | Arai et al. | 378/39 |
| 6,829,326 B2 | * | 12/2004 | Woods et al. | 378/38 |
| 7,103,141 B2 | * | 9/2006 | Sonobe et al. | 378/39 |
| 2004/0190678 A1 | * | 9/2004 | Rotondo et al. | 378/38 |
| 2005/0117693 A1 | * | 6/2005 | Miyano | 378/4 |
| 2006/0233301 A1 | | 10/2006 | Erhardt et al. | |
| 2006/0256921 A1 | * | 11/2006 | Tachibana et al. | 378/116 |
| 2007/0030951 A1 | * | 2/2007 | Park et al. | 378/38 |
| 2007/0183567 A1 | * | 8/2007 | Rotondo et al. | 378/38 |
| 2007/0269001 A1 | * | 11/2007 | Maschke | 378/38 |
| 2007/0297564 A1 | * | 12/2007 | Rotondo et al. | 378/39 |
| 2008/0165923 A1 | * | 7/2008 | Muller | 378/20 |
| 2009/0022270 A1 | * | 1/2009 | Yoshimura et al. | 378/19 |

FOREIGN PATENT DOCUMENTS

| | | |
|---|---|---|
| EP | 1457155 | 9/2004 |
| JP | 08-019534 | 1/1996 |
| JP | 13-258876 | 9/2001 |
| JP | 16-208754 | 7/2004 |
| WO | WO2004/014232 | 2/2004 |

* cited by examiner

*Primary Examiner* — Edward Glick
*Assistant Examiner* — Anastasia Midkiff
(74) *Attorney, Agent, or Firm* — Occhiuti Rohlicek & Tsao LLP

(57) ABSTRACT

A dental complex imaging system includes a base and chair on the base for allowing a patient sit; a base-mounted pole adjacent to the chair; a support part extending toward the patient; an expanding and contracting part pivotally coupled to the support part; a radiation generator that moves with the part for emitting radiation for an imaging mode selected from cephalography, panoramic radiography, and CT scanning; a detector disposed on the other side of the part and opposed to the generator; and a controller for reading imaging information, wherein the generator is disposed to slide to adjust a distance between itself and the detector according to the imaging mode while the patient sits on the chair.

17 Claims, 10 Drawing Sheets

COMPLEX IMAGING SYSTEM FOR DENTAL

CROSS-REFERENCE TO RELATED APPLICATIONS

This application is the National Phase of International Application No. PCT/KR2007/004667 filed Sep. 21, 2007, which claims the priority of PCT Application No. PCT/KR2006/003763, filed on Sep. 22, 2006. The contents of both applications are hereby incorporated by reference in their entirety.

TECHNICAL FIELD

The present invention relates to a dental complex imaging system, and more particularly, to a dental complex imaging system, which can conduct computed tomography (CT) imaging, panoramic radiography, and cephalography with one system.

BACKGROUND ART

In general, in the field of dentistry, using a dental X-ray imaging system for dental treatment or orthodontics, various imaging methods have been utilized, for instance, a panoramic radiography image scanning of the entire structure of teeth and the alveolar bone, a cephalometric image scanning of areas ranging from the front to the rear and ranging from the rear to the front of a patient's head and jawbone, and of the left side and the right side of the patient's head and jawbone, and a method of imaging the patient's oral cavity by irradiating a narrow x-ray beam to the patient's oral cavity from the outside after inserting a small sensor (intraoral sensor) for receiving the x-ray beam.

The panoramic image allows a user to observe the whole areas of the teeth and the alveolar bone in plane, but has a problem in that it is difficult to distinguish a minute forward or backward inclination of the teeth or a partial malocclusion in teeth arrangement. The cephalometric images can make up for the weak points of the panoramic images, but has a problem in that it is impossible to grasp the whole areas of the teeth and the jawbone at once.

So, since the panoramic image and the cephalometric image are simultaneously utilized because of their complementary features, the tendency is toward an increase in using a dental x-ray imaging system, that a detector for cephalogram is mounted on a panoramic x-ray imaging system to thereby scan the cephalometric image using the panoramic x-ray imaging system.

In the meantime, the panoramic image and the cephalometric image use 2-dimensional projection data. So, they generate an image-overlapping phenomenon because of a simple 2-dimensional projection image, and so, cause a difficulty in diagnosis of dental diseases. Recently, a 3-dimensional computed tomography (CT) imaging system has been developed and spread.

The dental CT imaging is to obtain a tomographic image of the inside of a thing to be scaned by mathematically reconstructing projection data of several tens to several hundreds around the thing using a computer.

DISCLOSURE OF INVENTION

Technical Problem

The dental CT imaging apparatus and the panoramic radiography apparatus according to prior arts are exclusively used for their own functions.

That is, in order to scan a patient's cephalometric image after imaging a CT image and a panoramic image, the patient has to move to a position where the cephalometric image can be obtained or a operator has to mount an additional apparatus to the imaging apparatus.

So, the operator and the patient suffers from an inconvenience of having to move to positions where the CT imaging apparatus, the panoramic radiography apparatus and the cephalography apparatus are respectively located, or additionally mount a new apparatus to each apparatus.

Technical Solution

Accordingly, the present invention has been made to solve the above-mentioned problems occurring in the prior arts, and it is an object of the present invention to provide a dental complex imaging system, which can conduct computed tomography (CT) imaging, panoramic radiography, and cephalography with one system without a position movement of a operator and a patient.

Advantageous Effects

The dental complex imaging system according to the present invention can provide a doctor and a patient with convenience and economic profits since it does not need various equipments for conducting CT imaging, panoramic radiography, and cephalography.

BEST MODE FOR CARRYING OUT THE INVENTION

To achieve the above objects, the present invention provides a dental complex imaging system comprising: a base seated on the ground; a chair part disposed on the upper portion of the base for allowing a patient to wait for imaging with him/her seated thereon; a pole mounted on the base so as to be adjacent to the chair part; a support part adapted to extend toward the patient from the top of the pole; an expanding and contracting part pivotally coupled to the underside of the support part so as to be expanded and contracted; a radiation generator part disposed below one side of the expanding and contracting part and moving according to expansion and contraction of the expanding and contracting part for emitting radiation selected according to computed tomography (CT) imaging, cephalography and panoramic radiography; a radiation detecting part disposed on the other side of the expanding and contracting part in such a way as to be opposed to the radiation generator part for detecting radiation selectively emitted from the radiation generator part according to the CT imaging, the cephalography and the panoramic radiography; and a control part for reading imaging information detected by the radiation detecting part.

The support part includes: a housing adapted to form the outward appearance thereof and having an elongated hole formed on the lower surface thereof for allowing the expanding and contracting part to be connected to the support part; and an expanding and contracting part driver disposed inside the housing of the support part for straightly moving the rotational center of the expanding and contracting part.

The expanding and contracting part driver includes: a conveyance body connected to the rotational center of the expanding and contracting part for rotating the expanding and contracting part; a guide coupled to a side of the conveyance body for guiding a straight reciprocating path of the conveyance body; and a conveying part coupled to the other side of the conveyance body for straightly reciprocating the conveyance body guided by the guide.

When the CT imaging is conducted, the expanding and contracting part driver fixes a straight reciprocation of the conveyance body and rotates just the expanding and contracting part, so that the radiation generator part and the radiation detecting part disposed below the expanding and contracting part form a circular orbit.

When the panoramic radiography is conducted, the expanding and contracting part driver straightly reciprocates the conveyance body and rotates the expanding and contracting part, so that the radiation generator part and the radiation detecting part disposed below the expanding and contracting part form an elliptical orbit.

When the cephalography is conducted, the expanding and contracting part driver fixes the conveyance body in its straight reciprocating motion and also fixes the expanding and contracting part in its rotation.

The expanding and contracting part includes: a fixed terminal rotatably coupled to the rotational center of the expanding and contracting part driver by the support part in such a way that the radiation detecting part is located below the fixed terminal; an expandable terminal slidably mounted with respect to the fixed terminal in such a way that the radiation generator part is located below the expandable terminal; and a guide bar disposed at both inner sides of the fixed terminal and both outer sides of the expandable terminal for guiding an expansion and contraction path of the expandable terminal.

The radiation generator part includes: a radiation source for generating radiation; and a radiation collimator for selectively changing a cross part of radiation generated from the radiation source and selectively emitting the radiation according to the CT imaging, the cephalography and the panoramic radiography.

The radiation collimator includes: a shutter body made of a lead (Pb) material, and having a CT imaging slit for emitting radiation necessary for the CT imaging when the CT imaging is conducted, a cephalography slit for emitting radiation necessary for the cephalography when the cephalography is conducted, and a panoramic radiography slit for emitting radiation necessary for the panoramic radiography when the panoramic radiography is conducted; and a pair of vertical guides coupled to both sides of the shutter body 163 in a slidably movable manner for slidably moving the shutter body in a vertical direction.

The radiation detecting part includes: a slide bar extended from the lower portion of the expanding and contracting part; an elevation body disposed on the slide bar in a slidably movable manner; an elevating part disposed between the slide bar and the elevation body for vertically conveying the elevation body along the slide bar; and a rectangular detector rotatably disposed on a side of the elevation body opposed to the radiation generator part.

The radiation detecting part further includes: a bracket mounted on a side of the elevation body; a detector rotatably disposed on the bracket; and a rotary motor disposed on the bracket for rotating the detector.

When the CT imaging is conducted, the detector is located in a horizontal state, and obtains an image emitted from the radiation generator part according to the rotation of the expanding and contracting part.

When the CT imaging is conducted, the detector is vertically moved to a position for conducting the CT imaging, and detects radiation to obtain an image of a wanted area.

When the cephalography is conducted, the detector detects the radiation emitted from the radiation generator part in an area corresponding to a detection area of the detector while being vertically conveyed like the elevation body conveyed along the slide bar, and vertically moves as long as the area corresponding to the detection area of the detector to obtain an image of the patient's entire head.

When the panoramic radiography is conducted, the detector is vertically rotated, and detects radiation emitted from the radiation generator part using some arrays of the detector according to the rotation of the expanding and contracting part.

Mode for the Invention

Referring to the attached drawing, a dental complex imaging system according to the present invention will be described in detail.

In description of the present invention, the names of components are defined in consideration of functions of the present invention, and so it is to be appreciated that the names are not understood in a sense to restrict the technical components of the present invention and the names could be called different names by those skilled in the art. In addition, the reference numerals of the components are attached for convenience in description, and illustrated contents in the drawings having the reference numerals are not restrict the components within a range of the drawings. Moreover, if there are functional similarity and sameness of the components, they can be considered as an equal configuration even though a modification is adopted.

First, referring to the attached drawings, the dental complex imaging system according to the present invention will be described in brief.

Figure 1:
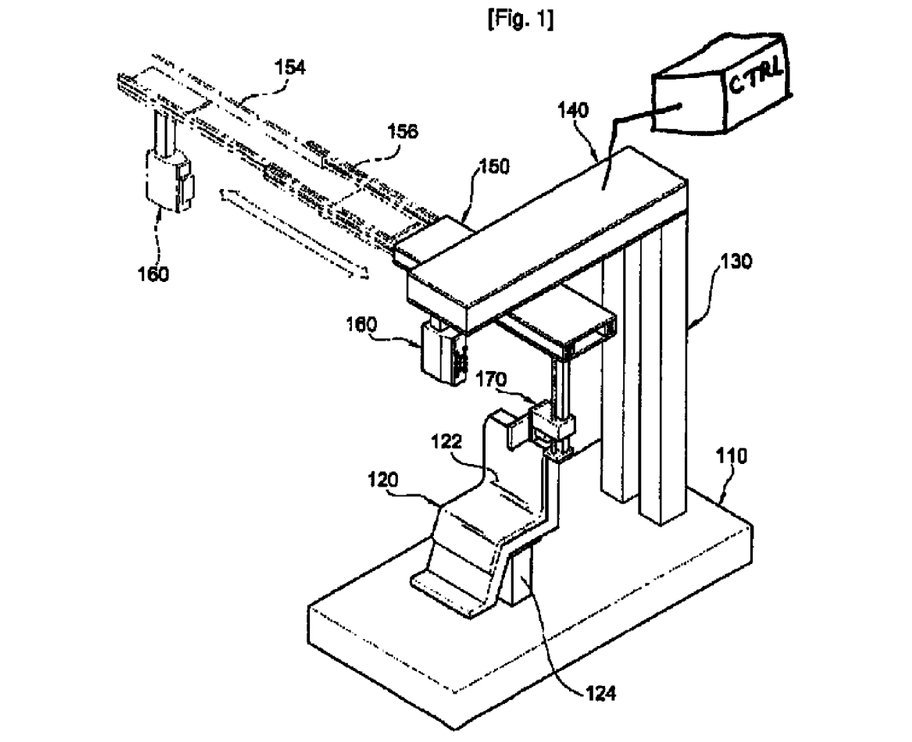
FIG. 1 is a perspective view of a dental complex imaging system according to the present invention.

FIG. 1 is a perspective view of the dental complex imaging system according to the present invention.

As shown in the drawing, the dental complex imaging system 100 according to the present invention includes: a base 110 seated on the ground; a chair part 120 disposed on the upper portion of the base 110 for allowing a patient (not shown) to wait for imaging with him/her seated thereon; a pole 130 mounted on the base 110 so as to be adjacent to the chair part 120; a support part 140 adapted to extend toward the patient from the top of the pole 130; an expanding and contracting part 150 pivotally coupled to the underside of the support part 140 so as to expanded and contracted in a longitudinal direction; a radiation generator part 160 disposed below one side of the expanding and contracting part 150 and moving according to expansion and contraction of the expanding and contracting part 150 for emitting radiation selected according to computed tomography (CT) imaging, cephalography and panoramic radiography; a radiation detecting part 170 disposed on the other side of the expanding and contracting part 150 in such a way as to be opposed to the radiation generator part 160 for detecting radiation selectively emitted from the radiation generator part 160 according to the CT imaging, the cephalography and the panoramic radiography; and a control part (not shown) for controlling operations of the above parts and reading imaging information detected by the radiation detecting part 170.

The base 110 is to separate and fix the chair part 120 and the support part 140 at a fixed interval from each other, and may be constructed of a plate type. However, if necessary, the chair part 120 and the support part 140 may be mounted on the floor of a building. Alternatively, the chair part 120 may be mounted on the floor of the building, but the support part 140 may be mounted on a wall surface of the building.

The chair part 120 allow the patient, who waits for the CT imaging, the cephalography and the panoramic radiography, to sit thereon, and includes a chair 122 for allowing the patient to sit thereon and an elevation device 124 for adjusting a height of the chair 120 according to the patient's physical conditions. The elevation device 124 may include a motor, which is electrically controlled, and an elevator, and it is preferable that the elevation device 124 is controlled by the control part (not shown).

In the meantime, the chair part 120 may further include a support (not shown) mounted on the top of the back thereof for supporting the patient's back of the head. Moreover, the support of the chair part 120 may be mounted on the back of the chair 122 or fixed below a rotational center of the support part 140, which will be described later, in such a way as to fix the patient's head by being rotated against the support part 140. The support of the chair can be changed by one of various embodiments, and so, its detailed description will be omitted.

The pole 130 is fixed on a side of the base 110 for supporting the support part 140, namely, supports the support part 140 at a height corresponding to a height of the head of the patient, who sits on the chair part 120. Furthermore, the pole 130 may include an elevator (not shown) for adjusting a height of the support part 140 supported on the top of the pole 130. The elevator of the pole 130 can adjust heights of the radiation generator part 160 and the radiation detecting part 170 disposed on the expanding and contracting part 150 in correspondence with the height of the head of the patient.

An end of the support part 140 is supported on the top of the pole 130 for supporting the expanding and contracting part 150 to thereby rotate the expanding and contracting part 150 in a circular or elliptical orbit.

Figure 2:
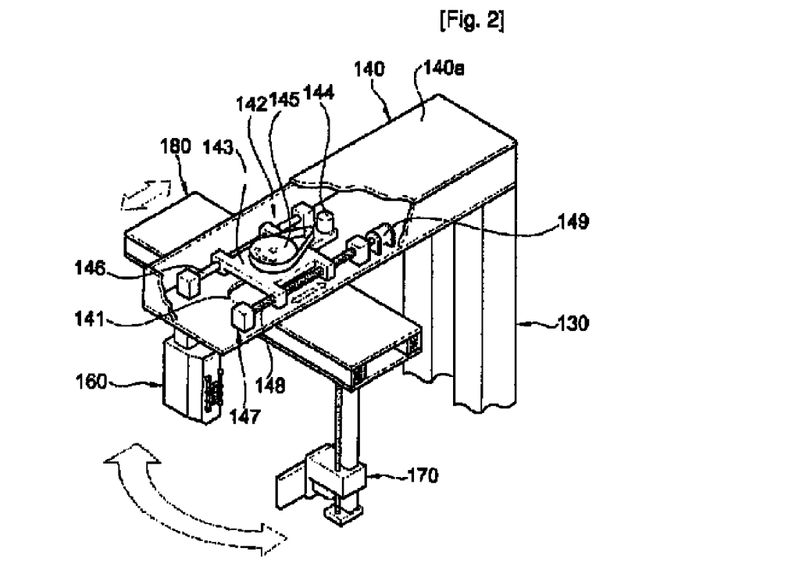
FIG. 2 is a perspective view of a support part of the dental complex imaging system according to the present invention.

Hereinafter, referring to FIG. 2, the support part 140 will be described in detail. FIG. 2 is a perspective view of the support part 140 of the dental complex imaging system 100 according to the present invention.

As shown in FIG. 2, the support part 140 of the dental complex imaging system 100 includes: a housing 140a forming the outward appearance thereof and having an elongated hole 141 formed on the lower surface thereof for allowing the expanding and contracting part 150 to be connected to the support part 140; and an expanding and contracting part driver 142 disposed inside the housing 140a for rotating or straightly moving the expanding and contracting part 150.

Here, the expanding and contracting part 150 rotates the expanding and contracting part 150 and simultaneously moves the rotational center of the expanding and contracting part 150 in a straight direction to thereby make the orbits of the radiation generator part 160 and the radiation detecting part 170, which are disposed at both ends of the expanding and contracting part 150, in a circular form or an elliptical form.

The expanding and contracting part driver 142 includes: a conveyance body 143 connected to the rotational center of the expanding and contracting part 150 for rotating the expanding and contracting part 150; a guide 146 coupled to a side of the conveyance body 143 for guiding a transfer path of the conveyance body 143; and a conveying part 147 coupled to the other side of the conveyance body 143 for conveying the conveyance body 143 guided by the guide 146. here, the conveyance body 143 includes a rotary motor 144 for rotating the expanding and contracting part 150 and a power transferring device 145, such as a belt and a pulley, for transferring driving power of the rotary motor to a rotary shaft (not shown) of the expanding and contracting part 150. The conveying part 147 includes a horizontal ball screw 148, to which the conveyance body 143 is coupled conveyably, and a horizontal conveying motor 149 for giving a rotational force to the horizontal ball screw 148.

So, the radiation generator part 160 and the radiation detecting part 170 form the circular orbit while the expanding and contracting part 150 is rotated by the operation of the rotary motor 144, and are rotated in such a way as to form the elliptical orbit while the conveyance body 143 performs a straight reciprocating motion.

The expanding and contracting part 150 is rotated in a state where it is connected to the expanding and contracting part driver 142, and reduces a distance between the radiation generator part 160 and the radiation detecting part 170 during the CT imaging and the panoramic radiography, but enlarges the distance between the radiation generator part 160 and the radiation detecting part 170 during the cephalography.

Figure 3:
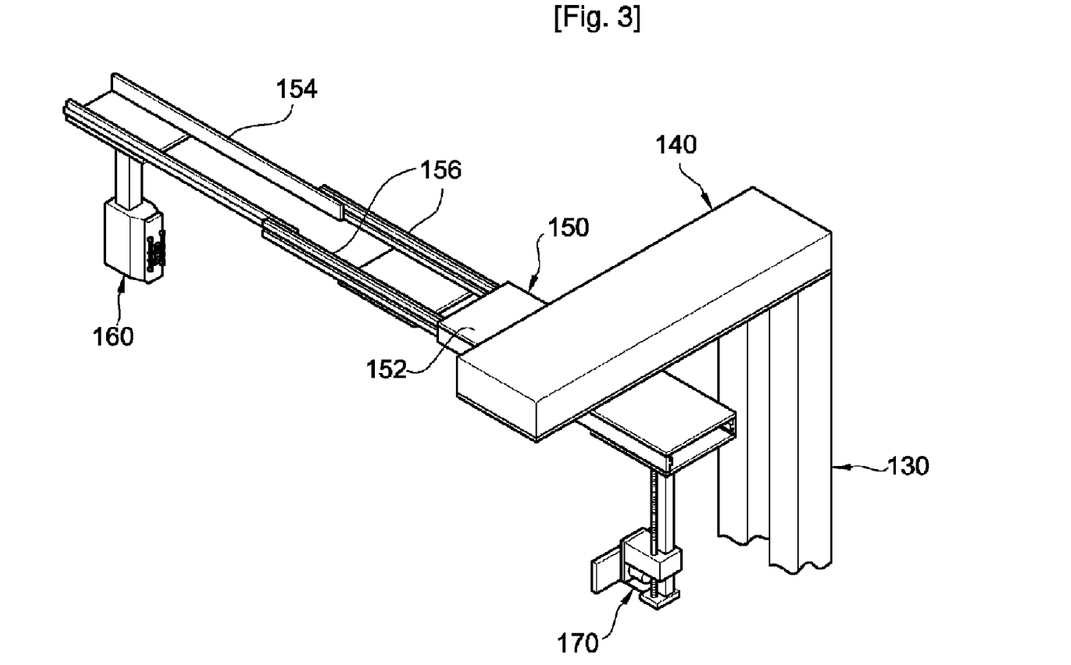
FIG. 3 is a perspective view of an expanding and contracting part of the dental complex imaging system according to the present invention.

Hereinafter, referring to FIG. 3, the expanding and contracting part 150 will be described in detail. FIG. 3 is a perspective view of the expanding and contracting part 150 of the dental complex imaging system according to the present invention.

As shown in FIG. 3, the expanding and contracting part 150 of the dental complex imaging system according to the present invention includes: a fixed terminal 152 coupled to the rotational center of the expanding and contracting part driver 142 of the support part 140 in such a way that the radiation detecting part 170 is located below the fixed terminal 152; an expandable terminal 154 slidably mounted with respect to the fixed terminal 152 in such a way that the radiation generator part 160 is located below the expandable terminal 154; and a guide bar 156 disposed at both inner sides of the fixed terminal 152 and both outer sides of the expandable terminal 154 for guiding an expansion and contraction path of the expandable terminal 154.

Here, the fixed terminal 152 has a predetermined length, is formed in a case type, and includes a rotary shaft (not shown) formed at the upper central portion thereof in such a way as to pass through the elongated hole 141 of the support part 140 and be coupled to the expanding and contracting part driver 142 of the support part 140.

The guide bar 156 disposed at both inner sides of the fixed terminal 152 has a pair of LM guides oppositely coupled to the inner sides of the fixed terminal 152. The fixed terminal 152 has rails formed on both inner sides thereof and coupled with the LM guides, and the expandable terminal 154 also has rails formed on both outer sides thereof and coupled with the LM guides. So, a distance of the expandable terminal 154 expanded and contracted against the fixed terminal 152 can be increased up to thrice as long as a length of the fixed terminal 152. However, the distance between the fixed terminal 152 and the expandable terminal 154 is not restricted to the above, and can be adjusted as occasion demands.

The radiation generator part 160 is to selectively emit radiation necessary for CT imaging, cephalography and panoramic radiography when the CT imaging, the cephalography and the panoramic radiography are conducted.

Figure 4:
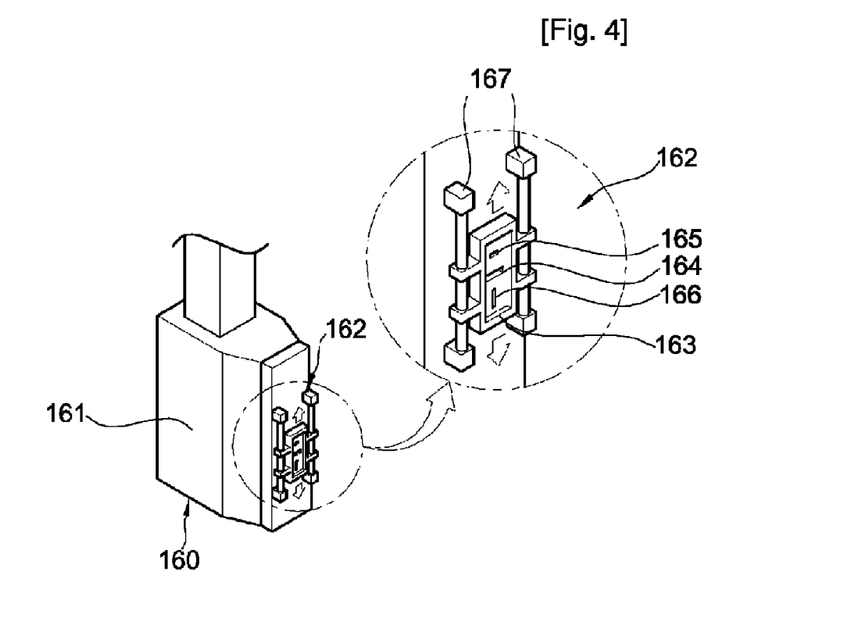
FIG. 4 is a perspective view of a radiation generator part of the dental complex imaging system according to the present invention.

Hereinafter, referring to FIG. 4, the radiation generator part 160 will be described in detail. FIG. 4 is a perspective view of the radiation generator part of the dental complex imaging system according to the present invention.

As shown in FIG. 4, the radiation generator part 160 of the dental complex imaging system 100 according to the present invention includes: a radiation source 161 for generating radiation; and a radiation collimator 162 for selectively changing a cross part of radiation generated from the radiation source 161 and emitting radiation according to the CT imaging, the cephalography and the panoramic radiography.

Here, the radiation source 161 includes a generator, a high voltage supplier, and a cooler. The components of the radiation source 161 are well known, and so, their detailed description will be omitted.

The radiation collimator 162 is disposed on the radiation emitter (not shown) of the radiation source 161 for changing the cross part of the emitted radiation and emitting the radiation. The radiation collimator 162 is made of a lead (Pb) material to prevent a leakage of radiation, and includes a shutter body 163 having a number of radiation emitting slits, and a pair of vertical guides 167 coupled to both sides of the shutter body 163 in a slidably movable manner for slidably moving the shutter body 163 in a vertical direction.

Here, the shutter body 163 has a CT imaging slit 164 for emitting radiation necessary for the CT imaging when the CT imaging is conducted, a cephalography slit 165 for emitting radiation necessary for the cephalography when the cephalography is conducted, and a panoramic radiography slit 166 for emitting radiation necessary for the panoramic radiography when the panoramic radiography is conducted.

In the meantime, shapes of the slits 164, 165 and 166 can be modified as occasion demands, but in brief, the CT imaging slit 164 is formed in a horizontally elongated hole, the cephalography slit 165 is formed in a vertically rectangular shape, and the panoramic radiography slit 166 is formed in a vertically elongated hole.

The radiation detecting part 170 is to selectively detect the radiation selectively emitted from the radiation generator part 160 during the CT imaging, the cephalography and the panoramic radiography according to the CT imaging, the cephalography and the panoramic radiography.

Figure 5:
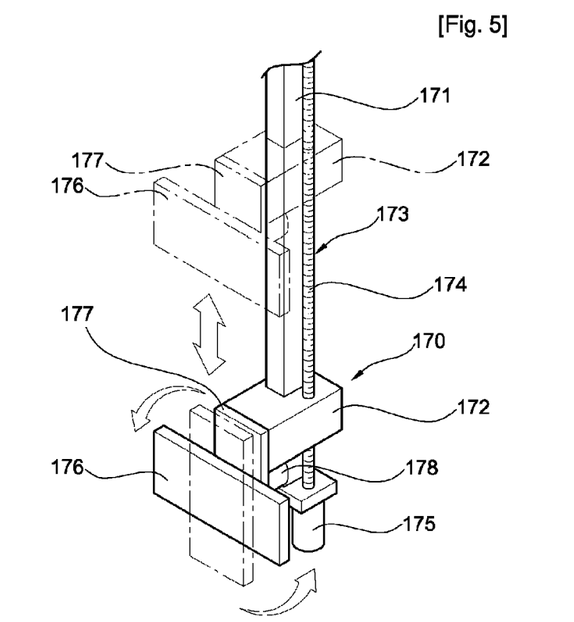
FIG. 5 is a perspective view of a detecting part of the dental complex imaging system according to the present invention.

Hereinafter, referring to FIG. 5, the radiation detecting part 170 will be described in detail. FIG. 5 is a perspective view of the radiation detecting part 170 of the dental complex imaging system according to the present invention.

As shown in FIG. 5, the radiation detecting part 170 of the dental complex imaging system 100 according to the present invention includes: a slide bar 171 extended from the lower portion of the fixed terminal 152 of the expanding and contracting part 150; an elevation body 172 disposed on the slide bar 171 in a slidably movable manner; an elevating part 173 disposed between the slide bar 171 and the elevation body 172 for vertically conveying the elevation body 172 along the slide bar 171; and a detector 176 rotatably disposed on a side of the elevation body 172 (side opposed to the radiation generator part 160).

Here, the elevating part 173 is to convey the elevation body 172, which is coupled to the slide bar 171 in the slidably movable manner, along the slide bar 171, and includes: a vertical ball screw 174 disposed in parallel with the slide bar 171; and a vertically driving motor 175 for transferring driving power to the vertical ball screw 174.

In addition, the detector 176 is rotatably disposed on a side of a bracket 177 mounted on a side of the elevation body 172, and a rotary motor 178 is disposed on the other side of the bracket 177 for rotating the detector 176. The detector 176 is in a rectangular form, keeps a horizontal state during the CT imaging and the cephalography but is vertically rotated during the panoramic radiography.

Here, the detector 176 is to detect radiation using various phenomena, such as ionization, chemical changes, generation of heat, formation of a track, exposure to light, and so on according to incidence of radiation, and uses an array X-ray sensing element, which can digitalize an amount of detected radiation. Since the array X-ray sensing element of the detector is well known, its detailed description will be omitted.

Now, the operation of the dental complex imaging system according to the present invention will be described in detail. Each component mentioned hereinafter should be understood in reference with the description and drawings.

Here, the dental complex imaging system according to the present invention can conduct the CT imaging, the cephalography, and panoramic radiography by a simple manipulation. Each imaging method will be described in detail.

First, referring to drawings, the CT imaging using the dental complex imaging system according to the present invention will be described in detail.

FIGS. 6 to 10 are views showing operational states during the CT imaging of the dental complex imaging system according to the present invention.

Figure 6:
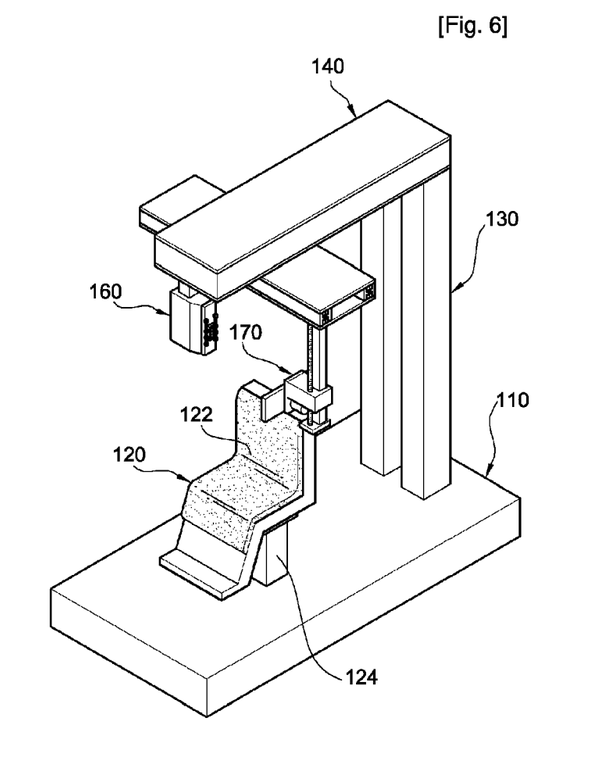
FIGS. 6 to 10 are views showing operational states during computed tomography (CT) imaging of the dental complex imaging system according to the present invention.
Figure 7:
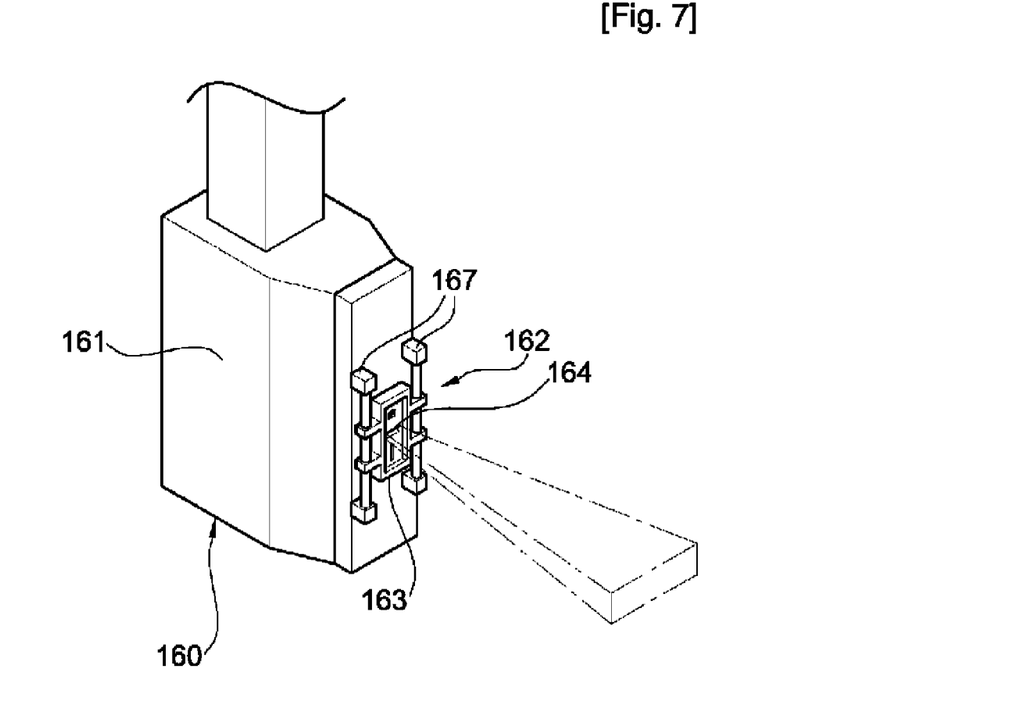
Figure 8:
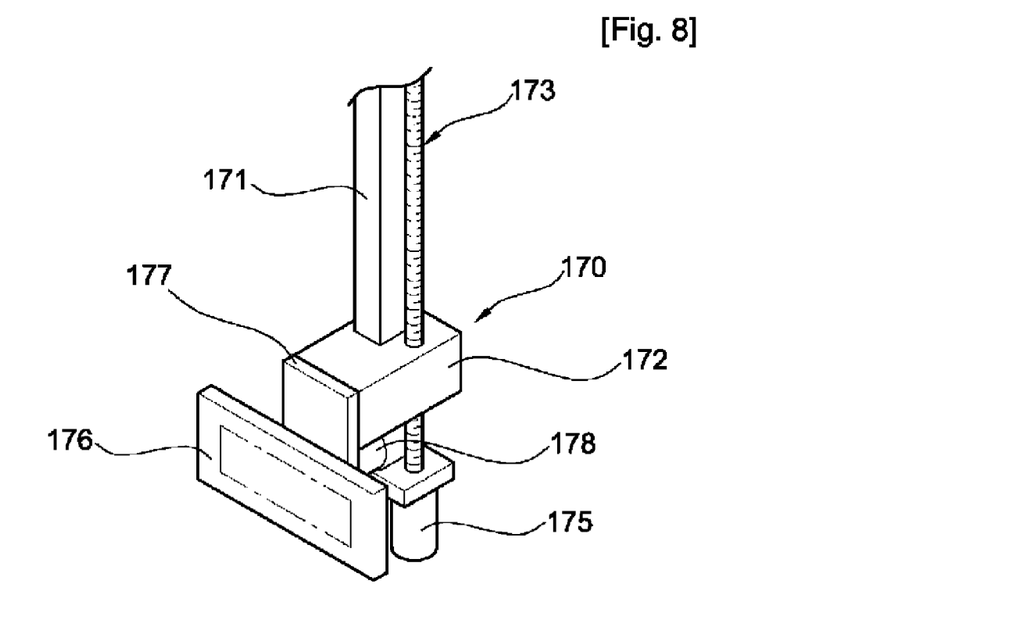
Figure 9:
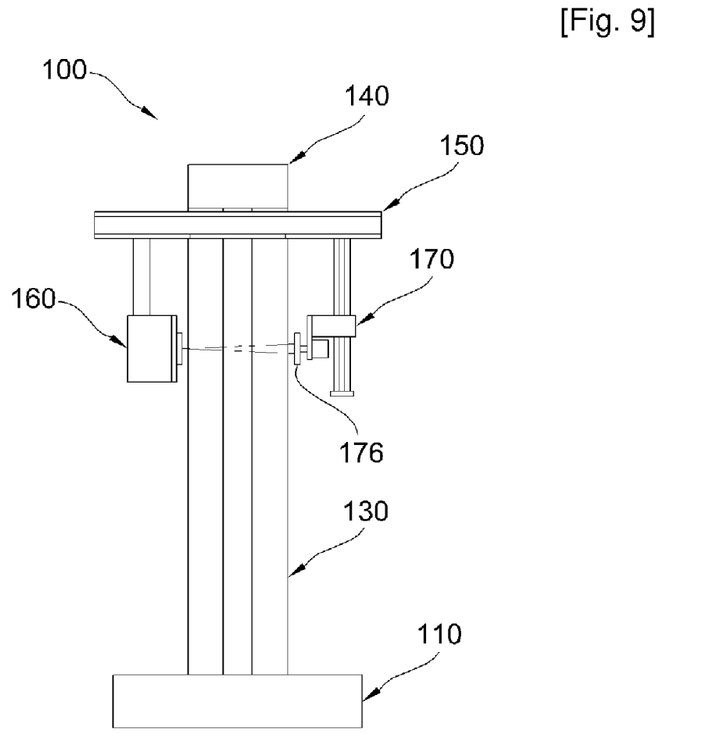
Figure 10:
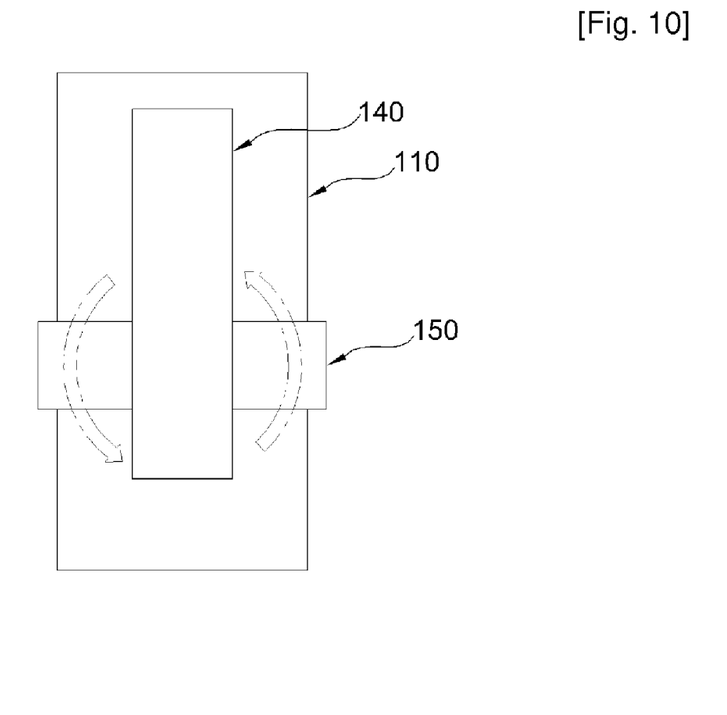

Here, FIG. 6 illustrates an installation state of the dental complex imaging system when the CT imaging is conducted, FIG. 7 illustrates a mounting state of the radiation generator part of the dental complex imaging system when the CT imaging is conducted, FIG. 8 illustrates a mounting state of the radiation detecting part of the dental complex imaging system when the CT imaging is conducted, and FIGS. 9 and 10 illustrate the interrelation between the radiation generator part and the radiation detecting part when the CT imaging is conducted.

As shown in FIG. 6, when the CT imaging is conducted, the expanding and contracting part 150 of the dental complex imaging system 100 is contracted, so that the distance between the radiation generator part 160 and the radiation detecting part 170 is kept in a contracted state for the CT imaging. In this instance, the chair part 120 is manipulated in such a way that the patient's head is located at the center of the radiation generator part 160 and the radiation detecting part 170.

In the meantime, the radiation collimator 162 of the radiation generator part 160 is located in such a way that the shutter body 163 is moved along the vertical guide 167 to emit radiation through the CT imaging slit 164 for the CT imaging. (See FIG. 7).

Moreover, the detector 176 of the radiation detecting part 170 is located in a horizontal state, and the elevation body 172, to which the detector 176 is coupled, is vertically conveyed to a position, where imaging is conducted, by the vertical ball screw 174 and the vertical driving motor 175 in such a way that a wanted portion is located at a radiation area. (See FIGS. 8 and 9)

Hereinafter, the expanding and contracting part 150 rotatably supported by the support part 140 is rotated by the expanding and contracting part driver 142 around the patient's head. In this instance, the conveyance body 143 of the expanding and contracting part driver 142 rotates 360 degrees in the circular orbit while it is fixed in its horizontal movement and the expanding and contracting part 150 is rotated by the rotary motor 144. (See FIG. 10)

According to the rotation of the expanding and contracting part 150, the CT imaging slit 164 of the radiation collimator 162 disposed on the radiation generator part 160 emits radiation, and the emitted radiation passes through the patient's head and is detected by the detector of the radiation detecting part 170. Meanwhile, data detected from the detector of the radiation detecting part 170 is read by the control part (not shown) and outputted through a display device (not shown).

Hereinafter, referring to drawings, a case that the cephalography is conducted using the dental complex imaging system according to the present invention will be described in detail.

FIGS. 11 to 14 are views showing operational states during cephalography of the dental complex imaging system according to the present invention.

Figure 11:
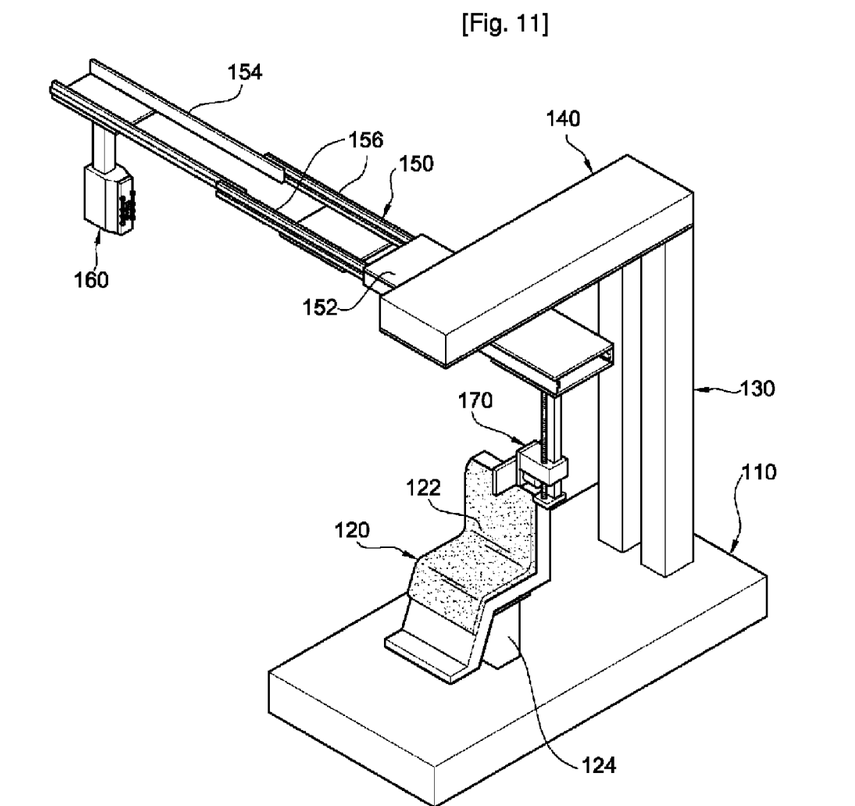
FIGS. 11 to 14 are views showing operational states during cephalography of the dental complex imaging system according to the present invention.
Figure 12:
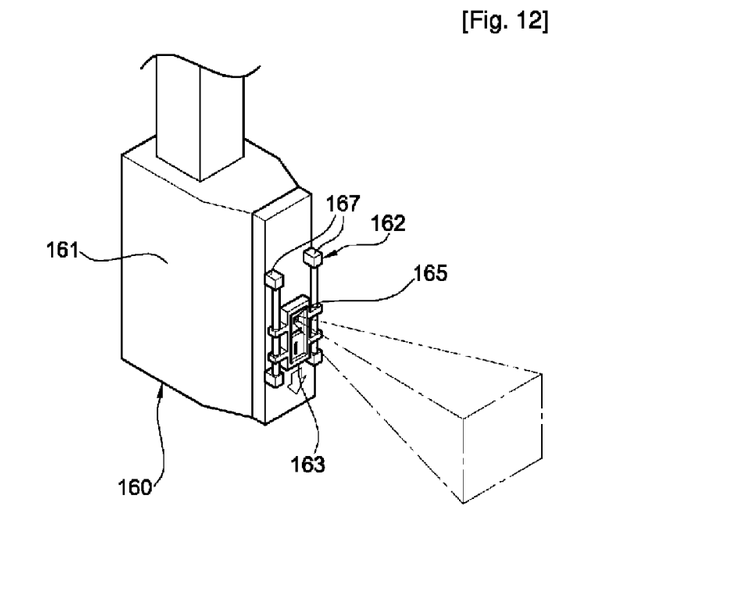
Figure 13:
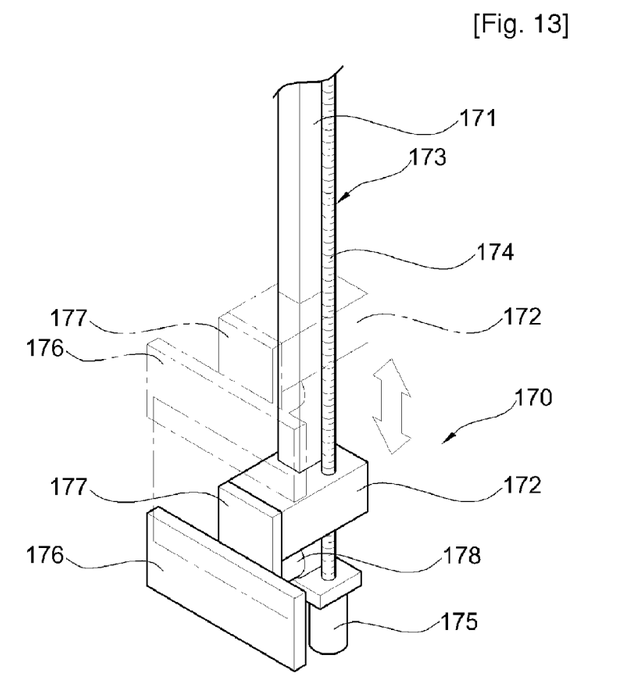
Figure 14:
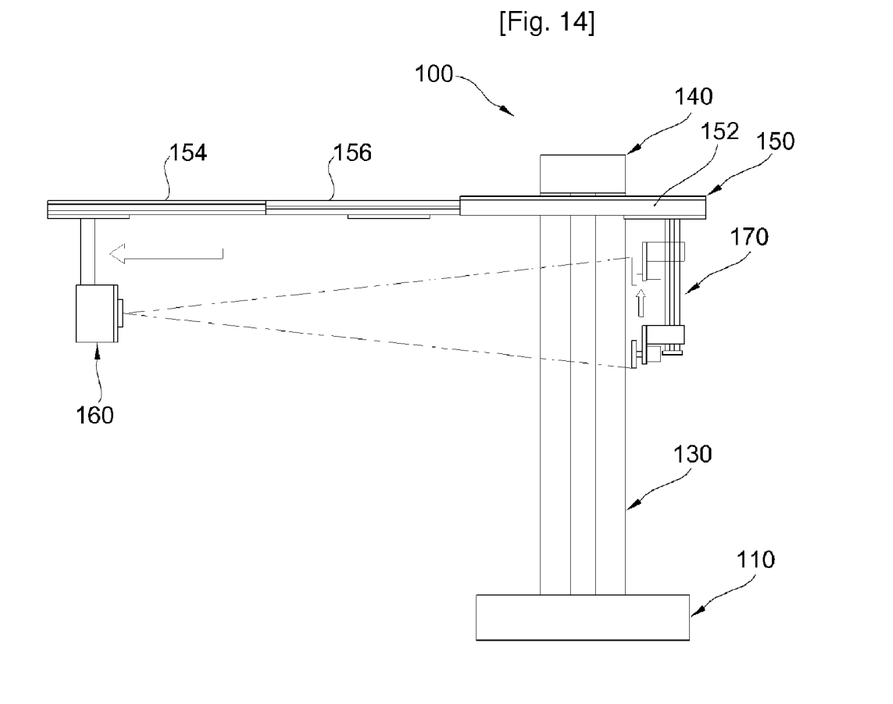

Here, FIG. 11 illustrates an installation state of the dental complex imaging system when the cephalography is conducted, FIG. 12 illustrates a mounting state of the radiation generator part of the dental complex imaging system when the cephalography is conducted, FIG. 13 illustrates a mounting state of the radiation detecting part of the dental complex imaging system when the cephalography is conducted, and FIG. 14 illustrates the interrelation between the radiation generator part and the radiation detecting part when the cephalography is conducted.

As shown in FIG. 11, when the cephalography is conducted, the expanding and contracting part 150 of the dental complex imaging system 100 is expanded, so that the distance between the radiation generator part 160 and the radiation detecting part 170 is widened as long as a distance for the cephalography (here, the distance means a distance between the cephalography slit 165 of the radiation generator part 160 and the surface of the detector 176 of the radiation detecting part 170, and may be 1,649 mm). In this instance, the chair part 120 is manipulated in such a way that the patient's head is located adjacent to the detector 176 of the radiation detecting part 170.

In the meantime, the radiation collimator 162 of the radiation generator part 160 is located in such a way that the shutter body 163 is moved along the vertical guide 167 to emit radiation through the cephalography slit 165 for the cephalography. (See FIG. 12).

Moreover, the detector 176 of the radiation detecting part 170 is located in a horizontal state, and the elevation body 172, to which the detector 176 is coupled, is vertically conveyed by the vertical ball screw 174 of the elevating part 173 and the vertical driving motor 175 in such a way as to conduct imaging while being conveyed upwardly from the lowermost portion (or downwardly from the uppermost portion) of a imaging area in synchronization with the cephalography slit 165 of the radiation generator part 160. (See FIG. 13)

So, the cephalography slit 165 of the radiation collimator 162 disposed on the radiation generator part 160 emits radiation, and the emitted radiation is emitted toward the radiation detecting part 170. At the same time, the elevation body 172 of the radiation detecting part 170 is moved in a vertically upward direction (or vertically downward direction) by the vertical ball screw 174 and the vertical driving motor 175 of the elevating part 173.

So, the detector 176 detects an area corresponding to a detection area, vertically moves to the area corresponding to the detection area of the detector 176, and detects radiation, which passes through the patient's head, by repeating the above.

Meanwhile, data detected from the detector of the radiation detecting part 170 is read by the control part (not shown) and outputted through a display device (not shown).

Hereinafter, referring to drawings, a case that the panoramic radiography is conducted using the dental complex imaging system according to the present invention will be described in detail.

FIGS. 15 to 19 are views showing operational states during panoramic radiography of the dental complex imaging system according to the present invention.

Figure 15:
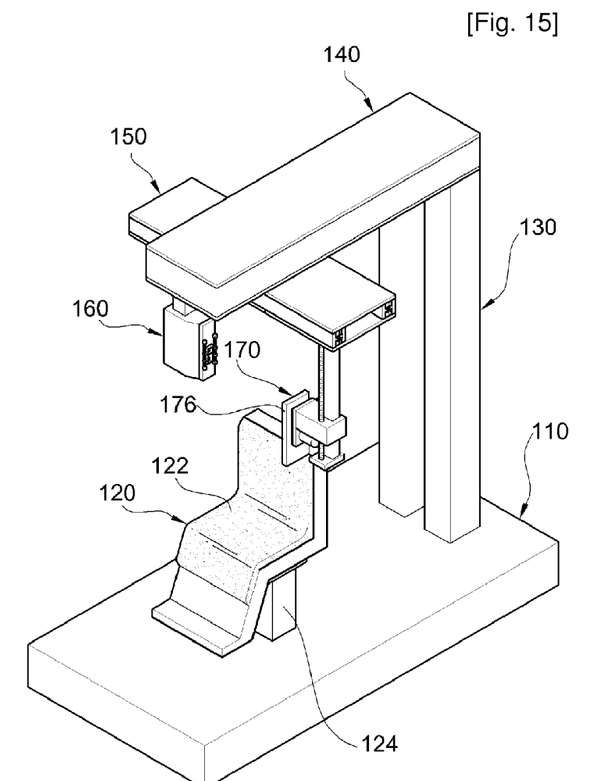
FIGS. 15 to 19 are views showing operational states during panoramic radiography of the dental complex imaging system according to the present invention.
Figure 16:
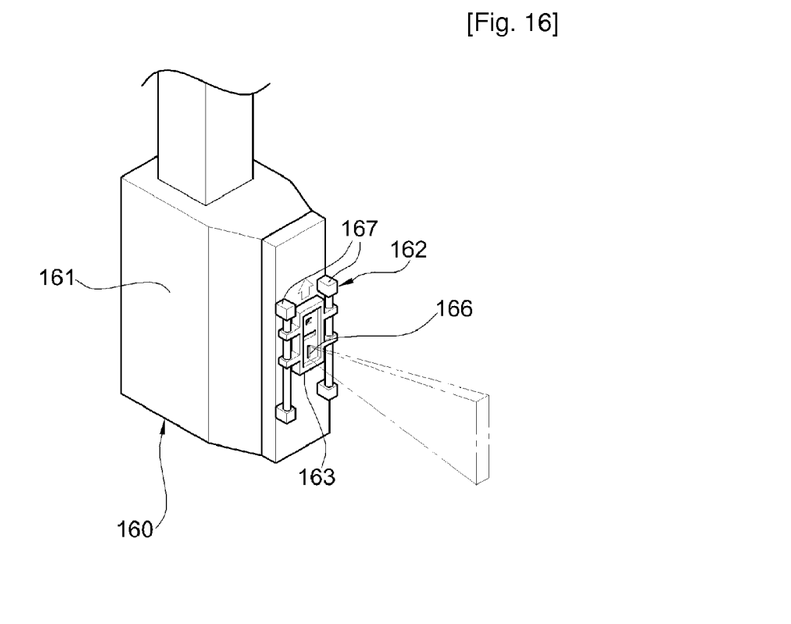
Figure 17:
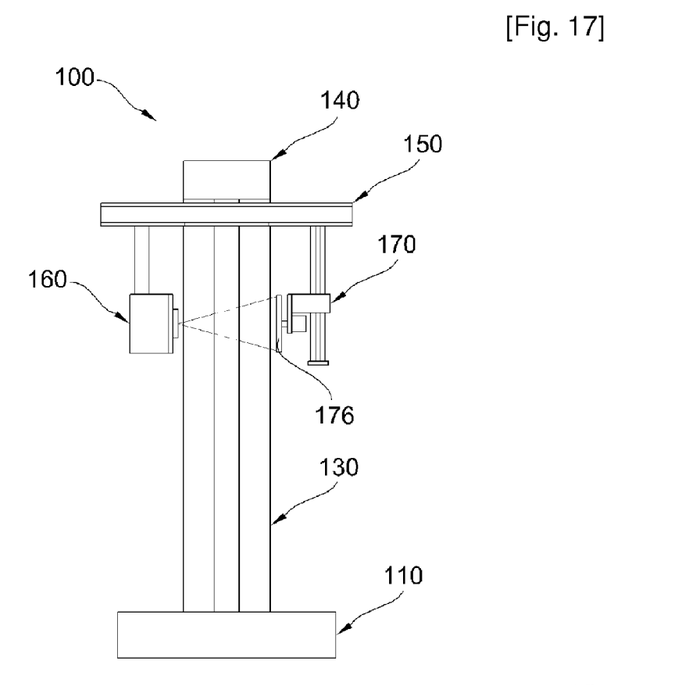
Figure 18:
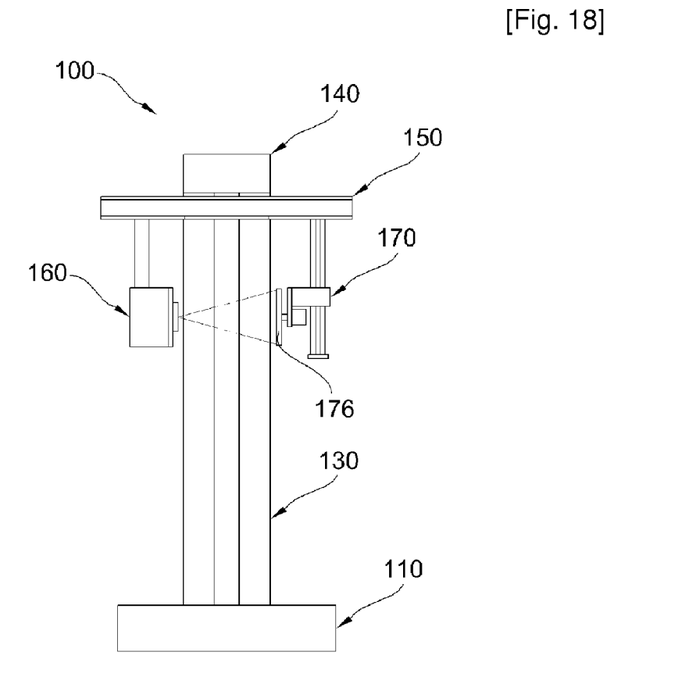
Figure 19:
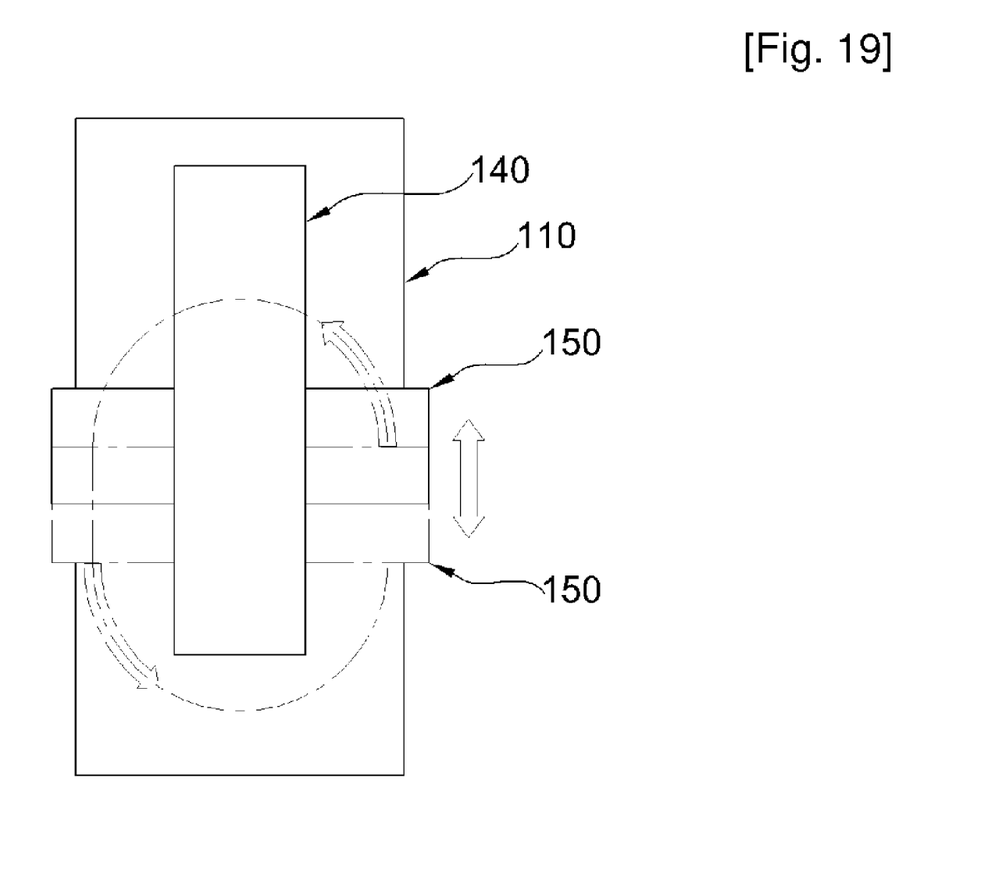

Here, FIG. 15 illustrates an installation state of the dental complex imaging system when the panoramic radiography is conducted, FIG. 16 illustrates a mounting state of the radiation generator part of the dental complex imaging system when the panoramic radiography is conducted, FIG. 17 illustrates an operational state of the radiation detecting part of the dental complex imaging system when the panoramic radiography is conducted, and FIGS. 18 and 19 illustrate the interrelation between the radiation generator part and the radiation detecting part when the panoramic radiography is conducted.

As shown in FIG. 15, when the panoramic radiography is conducted, the expanding and contracting part 150 of the dental complex imaging system 100 is contracted, so that the distance between the radiation generator part 160 and the radiation detecting part 170 is kept in a contracted state for the panoramic radiography. In this instance, the chair part 120 is manipulated in such a way that the patient's head is located adjacent to the detector 176 of the radiation detecting part 170.

In the meantime, the radiation collimator 162 of the radiation generator part 160 is located in such a way that the shutter body 163 is moved along the vertical guide 167 to emit radiation through the panoramic radiography slit 166 for the panoramic radiography. (See FIG. 16).

Moreover, the detector 176 of the radiation detecting part 170 is rotated by the rotary motor 178 and located in a vertically rotated state, and the elevation body 172, to which the detector 176 is coupled, is vertically conveyed by the vertical ball screw 174 and the vertical driving motor 175 in such a way that the lower end of the detector 176 and the lower end portion of radiation emitted from the radiation generator part 160 are coincided with each other. (See FIGS. 17 and 189)

Hereinafter, the expanding and contracting part 150 rotatably supported by the support part 140 is rotated by the expanding and contracting part driver 142 around the patient's head.

In this instance, the conveyance body 143 of the expanding and contracting part driver 142 rotates in the elliptical orbit while it horizontally reciprocates along the guide 146 by the horizontal ball screw 148 and the horizontal driving motor 149 and the expanding and contracting part 150 is rotated by the rotary motor 144 disposed on the conveyance body 143. (See FIG. 19)

According to the rotation of the expanding and contracting part 150, the panoramic radiography slit 166 of the radiation collimator 162 disposed on the radiation generator part 160 emits radiation, and the emitted radiation passes through the patient's head and is detected by the detector of the radiation detecting part 170. Meanwhile, data detected from the detector of the radiation detecting part 170 is read by the control part (not shown) and outputted through a display device (not shown).

In the meantime, when the panoramic radiography is conducted, it is possible that just some area of the detector 176 is selectively used to obtain data. The reason is that a general 2-dimensional (rectangular) detector has a frame speed for obtaining an image of generally less than 30 frames per a second, but a 1-dimensional line detector is used for obtaining a panoramic image.

So, the panoramic image can be obtained in such a way as to selectively use some area of the rectangular detector 176 (preferably, a vertically linear detection area 176) and process data detected from the selected detection area 176 at high speed. In addition, it is also possible to additionally mount a high speed data processing circuit (not shown) to process data detected in the selected detection area 176 at high speed.

Meanwhile, as described above, when the CT imaging, the cephalography and the panoramic radiography are conducted, the patient's scaned positions must be elevated according to the position of the radiation detecting part 170, and the position of the radiation detecting part 170 can be adjusted by the elevation device 124.

INDUSTRIAL APPLICABILITY

As described above, while the present invention has been described with reference to the particular illustrative embodiment, it is not to be restricted by the embodiment but only by the appended claims. It is to be appreciated that those skilled in the art can change or modify the embodiment without departing from the scope and spirit of the present invention.

For instance, additional components having additional functions can be added to the dental complex imaging system according to the present invention, or other components can be substituted with the components described in this embodiment. However, it is to be appreciated that all modifications belong to the technical category of the present invention if the modifications include the essential components of the present invention.

The invention claimed is:

1. A dental complex imaging system comprising:
a base seated on the ground;
a chair part disposed on the upper portion of the base for allowing a patient to wait for imaging with him/her seated thereon;
a pole mounted on the base so as to be adjacent to the chair part;
a support part adapted to extend toward the patient from the top of the pole;
an expanding and contracting part pivotally coupled to the underside of the support part so as to be expanded and contracted;
a radiation generator part disposed below one side of the expanding and contracting part and moving according to expansion and contraction of the expanding and contracting part for emitting radiation selected according to an imaging mode that includes cephalography and at least one of CT imaging and panoramic radiography;
a radiation detecting part disposed on the other side of the expanding and contracting part in such a way as to be opposed to the radiation generator part for detecting radiation selectively emitted from the radiation generator part according to the selected imaging mode; and
a control part for reading imaging information detected by the radiation detecting part,
wherein the radiation generator part is disposed to slide so as to adjust a distance between the radiation generator part and the radiation detecting part according to the imaging mode;
wherein two different imaging modes are performed consecutively while the patient remains positioned on the chair part
whereby the imaging system is capable of performing two different imaging modes sequentially while the patient remains positioned on the chair part.

2. The dental complex imaging system according to claim 1, wherein the support part comprises:
a housing adapted to form the outward appearance thereof and having an elongated hole formed on the lower surface thereof for allowing the expanding and contracting part to be connected to the support part; and
an expanding and contracting part driver disposed inside the housing of the support part for straightly moving the rotational center of the expanding and contracting part.

3. The dental complex imaging system according to claim 2, wherein the expanding and contracting part driver comprises:
a conveyance body connected to the rotational center of the expanding and contracting part for rotating the expanding and contracting part;
a guide coupled to a side of the conveyance body for guiding a straight reciprocating path of the conveyance body; and
a conveying part coupled to the other side of the conveyance body for straightly reciprocating the conveyance body guided by the guide.

4. The dental complex imaging system according to claim 3, wherein when CT imaging is conducted, the expanding and contracting part driver fixes a straight reciprocation of the conveyance body and rotates just the expanding and contracting part, so that the radiation generator part and the radiation detecting part disposed below the expanding and contracting part form a circular orbit.

5. The dental complex imaging system according to claim 3, wherein when panoramic radiography is conducted, the expanding and contracting part driver straightly reciprocates the conveyance body and rotates the expanding and contracting part, so that the radiation generator part and the radiation detecting part disposed below the expanding and contracting part form an elliptical orbit.

6. The dental complex imaging system according to claim 3, wherein when cephalography is conducted, the expanding and contracting part driver fixes the conveyance body in its straight reciprocating motion and also fixes the expanding and contracting part in its rotation.

7. The dental complex imaging system according to claim 1, wherein the expanding and contracting part comprises:
a fixed terminal rotatably coupled to the rotational center of the expanding and contracting part driver by the support part in such a way that the radiation detecting part is located below the fixed terminal;
an expandable terminal slidably mounted with respect to the fixed terminal in such a way that the radiation generator part is located below the expandable terminal; and
a guide bar disposed at both inner sides of the fixed terminal and both outer sides of the expandable terminal for guiding an expansion and contraction path of the expandable terminal.

8. The dental complex imaging system according to claim 1, wherein the radiation generator part comprises:
a radiation source for generating radiation; and
a radiation collimator for selectively changing a cross part of radiation generated from the radiation source and selectively emitting the radiation according to the selected imaging mode.

9. The dental complex imaging system according to claim 8, wherein the radiation collimator comprises:
- a shutter body made of a lead (Pb) material, and having
  - a CT imaging slit for emitting radiation necessary for CT imaging when CT imaging is conducted,
  - a cephalography slit for emitting radiation necessary for cephalography when cephalography is conducted, and
  - a panoramic radiography slit for emitting radiation necessary for panoramic radiography when panoramic radiography is conducted; and
- a pair of vertical guides coupled to both sides of the shutter body in a slidably movable manner for slidably moving the shutter body in a vertical direction.

10. The dental complex imaging system according to claim 1, wherein the radiation detecting part comprises:
- a slide bar extended from the lower portion of the expanding and contracting part;
- an elevation body disposed on the slide bar in a slidably movable manner;
- an elevating part disposed between the slide bar and the elevation body for vertically conveying the elevation body along the slide bar; and
- a rectangular detector rotatably disposed on a side of the elevation body opposed to the radiation generator part.

11. The dental complex imaging system according to claim 10, wherein the radiation detecting part further comprises:
- a bracket mounted on a side of the elevation body;
- a detector rotatably disposed on the bracket; and
- a rotary motor disposed on the b racket for rotating the detector.

12. The dental complex imaging system according to claim 10, wherein when CT imaging is conducted, the detector is located in a horizontal state, and detects radiation emitted from the radiation generator part according to the rotation of the expanding and contracting part.

13. The dental complex imaging system according to claim 10, wherein when cephalography is conducted, the detector detects the radiation emitted from the radiation generator part in an area corresponding to a detection area of the detector while being vertically conveyed like the elevation body conveyed along the slide bar, and detects the radiation while vertically moving as long as the area corresponding to the detection area of the detector.

14. The dental complex imaging system according to claim 10, wherein when panoramic radiography is conducted, the detector is vertically rotated, and detects radiation emitted from the radiation generator part according to the rotation of the expanding and contracting part.

15. The dental complex imaging system according to claim 10, wherein when panoramic radiography is conducted, the detector is vertically rotated, selectively uses a vertically linear detection area of the detector, and processes data detected in the selected detection area to obtain a panoramic image.

16. A dental complex imaging system comprising:
- a support for fixing a patient's head;
- a support part provided over the support;
- an expanding and contracting part rotatably coupled to the support part;
- a radiation generator part for emitting radiation according to an imaging mode that includes cephalography and at least one of CT imaging and panoramic radiography; and
- a radiation detecting part for detecting radiation emitting from the radiation generator part;
- wherein the radiation generator part and the radiation detecting part are disposed at both sides of the expanding and contracting part, and the radiation generator part is disposed to slide so as to adjust a distance between the radiation generator part and the radiation detecting part according to the imaging mode, and wherein two different imaging modes are performed consecutively while the patient remains stationary.

17. The dental complex imaging system according to claim 16, wherein the support is located below a rotational center of the expanding and contracting part.

* * * * *

UNITED STATES PATENT AND TRADEMARK OFFICE
CERTIFICATE OF CORRECTION

| | | |
|---|---|---|
| PATENT NO. | : 8,005,186 B2 | Page 1 of 1 |
| APPLICATION NO. | : 12/442136 | |
| DATED | : August 23, 2011 | |
| INVENTOR(S) | : Sang Chul Lee | |

It is certified that error appears in the above-identified patent and that said Letters Patent is hereby corrected as shown below:

Col. 12 lines 4-6
In claim 1, the last clause should read "whereby the imaging system is capable of performing the two different imaging modes sequentially."

Col. 14 Lines 27-34
In claim 16, the last clause should read
"wherein the radiation generator part and the radiation detecting part are disposed at both sides of the expanding and contracting part, and the radiation generator part is disposed to slide so as to adjust a distance between the radiation generator part and the radiation detecting part according to the imaging mode, and whereby the imaging system is capable of performing the two different imaging modes sequentially while the patient remains stationary."

Signed and Sealed this
Eighth Day of November, 2011

David J. Kappos
*Director of the United States Patent and Trademark Office*